(12) United States Patent
Munro, III et al.

(10) Patent No.: US 10,286,227 B2
(45) Date of Patent: *May 14, 2019

(54) RADIOACTIVE THERAPEUTIC DEVICE WITH FIXATION

(71) Applicant: SPEC MED Intellectual Property, LLC, St. Rose, LA (US)

(72) Inventors: John J. Munro, III, North Andover, MA (US); Matthew R. Hollows, Westminster, MA (US)

(73) Assignee: Spec Med Intellectual Property, LLC, St. Rose, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,905

(22) Filed: May 15, 2017

(65) Prior Publication Data

US 2017/0246476 A1    Aug. 31, 2017

Related U.S. Application Data

(63) Continuation of application No. 14/308,072, filed on Jun. 18, 2014, now Pat. No. 9,682,251.

(60) Provisional application No. 61/837,409, filed on Jun. 20, 2013.

(51) Int. Cl.
*A61N 5/10* (2006.01)

(52) U.S. Cl.
CPC .... *A61N 5/1007* (2013.01); *A61N 2005/1011* (2013.01); *A61N 2005/1024* (2013.01); *Y10T 29/49826* (2015.01)

(58) Field of Classification Search
CPC .......... A61N 5/1007; A61N 2005/1024; A61N 2005/1011; Y10T 29/49826
See application file for complete search history.

(56) References Cited

U.S. PATENT DOCUMENTS

| 6,293,899 B1 * | 9/2001 | Sioshansi | A61N 5/1001 600/3 |
| 2008/0177127 A1 * | 7/2008 | Allan | A61M 25/1002 600/7 |
| 2009/0030260 A1 * | 1/2009 | Mick | A61M 37/00 600/7 |
| 2010/0094074 A1 * | 4/2010 | Mark | A61M 25/10 600/3 |

(Continued)

FOREIGN PATENT DOCUMENTS

WO    WO 2004/026111 A2    4/2004

*Primary Examiner* — Christine H Matthews
*Assistant Examiner* — Joshua Daryl D Lannu
(74) *Attorney, Agent, or Firm* — Muirhead and Saturnelli, LLC

(57) ABSTRACT

Devices and techniques for permanent application of radioactive sources in the field of brachytherapy are described. In an embodiment, an implantable device for radiation therapy of pathological tissues directed toward the administration of radiation to tissue adjacent a cavity wall or surgical excision. The device may include an insertable member, such as a substantially cylindrical member, having at least two ends, a central section positioned between the ends, and a fixation element to retain the implantable device implanted in tissue at a desired position. The device may further include a radioactive source at least partially positioned within the insertable member and that is disposed to deliver radiation to a desired area.

19 Claims, 14 Drawing Sheets

(56) References Cited

U.S. PATENT DOCUMENTS

2011/0270012 A1* 11/2011 Miller .................. A61N 5/1001
600/7

* cited by examiner

RADIOACTIVE THERAPEUTIC DEVICE WITH FIXATION

RELATED APPLICATIONS

This application claims priority to U.S. Provisional App. No. 61/837,409, filed on Jun. 20, 2013, entitled "Radioactive Therapeutic Device with Fixation," which is incorporated herein by reference.

TECHNICAL FIELD

This application relates to the field of brachytherapy, particularly the field of radiation treatment of cancerous tissue that would occur in the body by placing radioactive sources in or near the cancerous tissue.

BACKGROUND OF THE INVENTION

Ionizing radiation is employed in the management of a wide variety of malignant tumors, providing a mechanism whereby the malignancy can be destroyed while the normal tissues are preserved. With preservation of normal tissues, normal function and normal appearance may also be preserved. Hence, ionizing radiation forms part of the treatment for over half of all patients with cancer. The overall effectiveness of radiation therapy, however, depends upon the balance between effective tumor control and morbidity due to the treatment. It is understood that the differential effects of ionizing radiation on tumors and normal tissues gives rise to a favorable therapeutic ratio for most patients. However, radiation can have destructive immediate and delayed effects on normal tissues. Techniques employed for radiation therapy significantly affect the incidence and severity of these destructive effects.

Various techniques have been developed to treat tumors in the body. In general, the use of radiation to reduce or eliminate malignancy has been known for many years. One of the major issues in all of the techniques is the prevention of damage to healthy tissue. Because all types of ionizing radiation affect tissues by means of the same basic physical mechanisms, differences in spatial or temporal distributions are responsible for different effects observed. The method for delivering radiation thus becomes highly significant.

The type of radiation treatment of malignant tumors most often performed involves directing a beam of radiation from a point external to the patient's body onto the area of the body in which the tumor is located, for the purpose of shrinking and ultimately destroying the tumor. This technique is known as "teletherapy" or external beam radiation therapy. Such treatment exposes normal healthy tissue to a high dose of radiation in the beam and consequently subjects the normal tissue to potential injury. Conventional external beam radiation treatments rely on multiple fractions of dose in order to ensure that the highest fractions of tumor cells are exposed at the most sensitive parts of the cell life cycle.

In contrast to external beam radiation therapy, brachytherapy is a method of radiation treatment of cancerous tissue in which the radioactive source is placed in or near the cancerous tissue. Because of the proximity of the radioactive source to the target tumor or cancerous tissue, brachytherapy treatment permits administration of a higher radiation dose to the tumor with better sparing of surrounding normal healthy tissues.

Because a delivered dose from a radioactive source decreases proportionately to the square of the distance from that source, brachytherapy permits the delivery of very high radiation doses to those areas of a tumor in close proximity to the source, with relative sparing of more distant tissues. With careful placement, so that the radioactive source is in proximity to the tumor or target tissue and distant from normal tissue, effective therapy against the tumor may be combined with minimal collateral damage to normal tissues.

Brachytherapy came into use as a treatment tool for cancer soon after the discovery of radium by Marie Curie in 1898. Goldberg and London used it for the treatment of facial basal cell carcinomas in 1903 with surface applicators. Brachytherapy can be applied to cancer either by permanent implantation or by temporary application of removable sources. Permanent implantation results in the radioactive source, or sources, being left in the body in perpetuity, delivering their radiation dose until the radioactive material in the source has completely decayed away.

A variety of radionuclides and methods for permanent or temporary implantation have been developed. For example, a variety of radioisotopes, including 125Iodine, 103Palladium, 198Gold 131Cesium, 137Cesium, 60Cobalt, 169Ytterbium and 192Iridium, have been used in the treatment of cancers involving such tissues as the breast, the prostate, the brain, lung, the head and neck, the female reproductive tract, the musculoskeletal system and related soft tissues, and the eye. Examples of radioactive sealed sources employed in brachytherapy and intended for permanent implantation are discussed in B. H. Heintz et al., "Comparison of 1-125 sources used for permanent interstitial implants," Medical Physics, Vol. 28, No. 4, April 2001, pp. 671-682, the contents of which are hereby incorporated by reference.

Certain devices known in the prior art are intended for insertion of brachytherapy sources directly into the tissues without employing a needle or other similar delivery device. An example of such a device may be found in the disclosure of U.S. Pat. No. 4,815,449 to Horowitz, which is incorporated herein by reference. This patent provides, in certain embodiments, an implant of sufficient rigidity to be driven into a tumor without deflection, so that the implant may be used independently of a positioning or delivery device.

Alternatively, brachytherapy sources may be positioned in the tissues to be treated by insertion through a delivery device, for instance, a needle. This technique is common, for example, in the treatment of prostate cancer. Using a delivery device may allow precise positioning of sources in areas requiring treatment. Brachytherapy sources from various manufacturers may be made to the same set of specifications so that they are compatible with those delivery systems in common use. In those delivery systems, the sources may be preloaded into needles or other delivery devices. The position of a plurality of sources within the delivery device may be maintained by placing loose spacers between the sources to establish and maintain a desired positioning. Once the sources are positioned in the delivery device, insertion into the tissues takes place. To insert the sources, the needle containing them must first be inserted to a preselected depth into the appropriate positioned in the patient's tissues.

An injection mechanism such as a mandrel may then be inserted into the needle with its distal end in contact with the linear array of sources. The needle, thereafter, may be withdrawn over the mandrel, leaving the sources and loose spacers resident in the preselected tissue area. Once positioned within the tissues using this method, the sources and loose spacers are free to move from their original position, as there are no constraints on the position or orientation of the sources other than the friction of the tissue itself in contact with the surfaces of the sources. Such movement can lead to the undesirable consequence that dose distribution within the tissue may be changed, for instance, movement of the sources after deployment can change the area being irradiated, and can change the dose being delivered both to the preselected tumor regions and to the surrounding normal tissues.

Numerous approaches to solve this problem have been developed. In order to maintain the radioactive sources and spacers in their appropriate relative positions, devices have been designed to join these sources and spacers together. Examples of such devices are described in U.S. Pat. No. 6,709,381 to Munro, U.S. Pat. No. 6,820,318 to Terwilliger et al. and U.S. Pat. No. 6,010,446 to Grimm, which are all incorporated herein by reference. These devices preserve the relative linear positioning of the multiple sources, but provide only limited resistance to longitudinal movement.

A number of approaches have been utilized to prevent further displacement of the sources. Examples include U.S. Pat. No. 8,114,007 to Lamoureux et al. and U.S. Pat. No. 8,366,598 to Lamoureux et al., which are incorporated herein by reference, which describe a source or sources molded within a polymeric material to encapsulate the radioactive sources and includes a plurality of protrusions on the outer surface of the encapsulating polymeric material to resist migration and rotation.

Another example is U.S. Pat. No. 4,936,823 to Colvin et al., which is incorporated herein by reference, which describes resilient arms which can be manipulated to anchor a body containing a radioactive source within a body canal. Further, U.S. Pat. No. 6,264,599 to Slater et al., which is incorporated herein by reference, describes a method similar to Colvin '823 except that Slater '599 provides for automatically positively engaging the resilient arms into the tissue.

All of these methods require substantial tissue surrounding the sources to prevent lateral movement and to provide resistance to the deployment of the resilient arms or the protrusions of the polymeric extrusions. Although these methods are, in many cases, sufficient when placing the brachytherapy source into massive tumor or tumor tissue itself surrounded by healthy tissue, there exist cases where treatment is desired after surgical removal/resection of the tumor.

Gross surgical removal of tumor tissue can leave behind traces of tumor, precancerous, or other diseased tissue which can foster recurrence or metastasis of the tumor. Accordingly, the site of removal of a tumor is often treated postoperatively in an attempt to destroy any such diseased tissue left behind by the surgery. Conventional techniques for treating the site of surgical removal of a tumor include post-operative administration of radiation, chemotherapy, and/or heat.

Although external beam therapy and short-range therapy are two commonly practiced techniques for administration of post-operative radiation, external beam is less desirable. In external beam therapy, also known as teletherapy, an external radiation beam is directed at the treatment site. In teletherapy, the radiation beam must be carefully positioned with respect to the treatment site to minimize the radiation exposure of the surrounding healthy tissue. Even with a high degree of precision, however, healthy tissue in the vicinity of the treatment site may receive significant doses of radiation. This side effect can be compounded when treatment requires repeated administrations, each requiring careful positioning of the radiation beam.

In short-range brachytherapy, radioactive sources are placed at or near the treatment site, i.e. the region adjacent to the surgical resection, to provide site-specific delivery of radiation therapy, potentially reducing undesirable side effects associated with teletherapy, such as irradiation of healthy tissue. One common brachytherapy technique uses catheters to deliver temporary radiation to the treatment site. In this technique, numerous catheters may be simultaneously inserted into or around the treatment site, sewn into place, loaded with solid isotopic pellets for a prescribed time, and then removed. The process of placing a number of catheters simultaneously within the appropriate region is cumbersome and time-intensive. Additionally, invasive insertion and external exposure of the catheters presents an increased risk of infection to the patient, and can result in significant discomfort for the patient during treatment. Finally, any subsequent treatment, for example, treatment following tumor recurrence, requires that the entire process be repeated from the beginning. For these reasons, temporary brachytherapy is not a desirable treatment method.

A common brachytherapy technique employs radioactive implants to deliver permanent radiation therapy. In this technique, numerous radioactive sources are implanted directly into or around the treatment site. However, as the tumor, in these cases, has already been surgically removed and the desired treatment is to the limited amount of tissue adjacent to the surgical resection, there is insufficient tissue in the region of the target to employ the methods described above, namely relying on the pressure of the surrounding tissue to render the irregular surface to be immobile, as described by Munro '381, Terwilliger '318, Grimm '446, Lamoureux '007, or Lamoureux '598, or to provide tissue around the source in all directions to provide means for resilient arms to engage, as described by Colvin '823 or Slater '599.

In limited cases, a device for providing radiation treatment to a treatment site that can be implanted at the time of tumor removal and which delivers a relatively uniform dose of radiation throughout the surrounding tissue as described by U.S. Pat. No. 6,527,693 to Munro et al., which is incorporated herein by reference. However, in many cases, such as the lung, the residual tissue remaining after resection and requiring treatment is irregularly shaped and cannot be treated using the method described by Munro '693.

Methods to affect this type of treatment have been described. Reference is made to W. Lee et al., "Limited resection for non-small cell lung cancer: observed local control with implantation of 125I brachytherapy seeds," Annals of Thoracic Surgery 75(1), January 2003, pp. 237-242, which is incorporated herein by reference, in which is described a brachytherapy technique that uses strands of ten 125Iodine seeds, embedded in polyglactin 910 suture with 1 cm spacing which were affixed by suture along the resection margin or 0.5 cm on either side of the margin. Reference is also made to A. Chen et al., "Intraoperative 125I brachytherapy for high-risk stage I non-small cell lung carcinoma," Int. J. Radiation Oncology Biol. Phys., Vol. 44, No. 5, 1999, pp. 1057-1063, which is incorporated herein by reference, in which is described an alternative method utilizing vicryl surgical mesh imbedded with stranded 125Iodine radioactive seeds placed over the tumor bed and surgical resection line and sutured in place. Both of these methods require manual suturing of the strands or mesh in place. The difficulty of precisely delivering the brachytherapy sources intraoperatively to achieve the proper dose distribution and minimizing the radiation dose to the clinicians performing the procedure make these techniques less desirable.

An improved method for delivering a brachytherapy source has been described in U.S. Pat. Nos. 7,604,586, 7,972,260, and 8,267,849, all to Wazer et al., which are incorporated herein by reference, in which the radioactive sources are incorporated directly into a subset of the surgical staples used in the procedure. In this way, the sources are secured in position directly adjacent to the surgical resection and are immobile. This method facilitates the precise placement of brachytherapy sources relative to the surgical margin, assures the seeds remain fixed in their precise position for the duration of the treatment, overcomes the technical difficulties of manipulating the seeds through the narrow surgical incision, and reduces the radiation dose to the clinicians. However, this method also has a number of drawbacks.

In particular, the concept of delivering the radioactive sources temporally and spatially adjacent to the surgical resection is of limited value. In practice, most procedures remove the suspected tumor tissue (and therefore remove the surgical stapling/resection device) and await pathological analysis before deciding to perform brachytherapy. Physicians do not want to introduce brachytherapy sources into the patient until it has been determined that the tissue is malignant. Therefore, the advantage of having the brachytherapy source delivery device physically aligned with the surgical stapling/resection device is lost.

The attachment of a brachytherapy source delivery device to the surgical resection device/stapler also has several other disadvantages. It provides a more cumbersome device for the surgeon to manipulate, and may introduce difficulties introducing the assembly through standard thoroscopic ports. It can also interfere with surrounding tissue, leaving less margin around the suspect tumor from which to excise. There is also risk that the brachytherapy source delivery device could dislodge from the surgical resection device/stapler, thereby complicating the procedure.

By design, "staple-like" brachytherapy sources are delivered on the active-lung side of the surgical staple line (as the surgical resection is immediately adjacent to the surgical staples on the other side). This requires the staple-like brachytherapy sources to pierce the lung, introducing the potential for air leakage. Furthermore, the strength of the closure of the staple-like brachytherapy sources is critical. As the lung cyclically inflates, it cyclically applies force to the source closure. If the closure is insufficient, the staples can become unattached and "free-floating." Furthermore, this force on the staple closure can cause damage to adjacent lung tissue, such as by tearing. This is particularly critical as the tissue is often diseased or pathologic.

The use of staple-like brachytherapy sources requires access to both sides of the tissue through which the source will be deployed. The staple-like brachytherapy sources are pushed through the tissue from one side and an anvil-like element is positioned on the opposite side to affect the bending and securing of the source. The amount of tissue between the two elements must be within a very narrow limited range in order for the staple-like brachytherapy sources to be properly bent and secured. If the tissue is too thick, or the anvil-like element does not assume the proper spacing, the staple-like brachytherapy sources can be incorrectly deformed and not secured, leaving them loose to move about the patient. This can also be a concern if there are areas where no tissue exists between the two elements of the brachytherapy delivery device. This will leave sources free-floating within the patient.

Accordingly, there remains a need for a system which can easily deploy and retain the brachytherapy sources in the desired treatment position adjacent to a surgical resection which alleviates the problems associated with the above-delineated systems.

SUMMARY OF THE INVENTION

According to the system described herein, an implantable device for brachytherapy includes an insertable member having at least two ends, a central section positioned between the ends, and a fixation element that retains the implantable device in an inserted position within tissue. A radioactive source is disposed within the insertable member. The fixation element may include a helical coil configuration of the insertable member, in which the helical coil configuration enables twisting of the insertable member for insertion of the implantable device in the tissue and to provide a desired positioning of the radioactive source. The insertable member may be made of a memory alloy, and the fixation element may include a first shape of the insertion member for insertion into the position within the tissue and a second shape into which the insertable member forms after insertion into the position. The memory alloy may include Nickel Titanium or nitinol. Alternatively and/or additionally, the fixation element may include at least one barbed protrusion, and/or a plurality of barbed protrusions, on at least one of the at least two ends of the insertable member. The fixation element may include a helical coil configuration of the insertable member, wherein the helical coil configuration enables twisting of the insertable member for insertion of the implantable device in the tissue and to provide a desired positioning of the radioactive source, and the insertable member may further include at least one barbed protrusion on at least one of the at least two ends of the insertable member. The radioactive source may be completely or partially encapsulated within the insertable member. The insertable member may include a chamber with at least one cut-out for external accessibility, and in which the radioactive source is partially encapsulated within the insertable by being disposed within the chamber with the at least one cut-out. The radioactive source may be encapsulated within the fixation element. The fixation element may include at least one barbed protrusion, and the radioactive element may be encapsulated within at least a portion of the barbed protrusion. The radioactive source may include a radioactive nuclide selected from at least one of: palladium-103, iodine-125, gadolinium-153, samarium-145, cesium-131 or ytterbium-169.

According further to the system described herein, a method of manufacturing an implantable device for brachytherapy includes forming an insertable member of the implantable device for insertion into an area of tissue. A radioactive source is encapsulated in the implantable device. A fixation element is incorporated into the insertable member for fixing the radioactive source at a desired location in the area of the tissue. The insertable member may be made of a memory alloy. The fixation element may be a helical coil configuration of the insertable member, and in which the helical coil configuration enables twisting of the insertable member for insertion of the implantable device into the area of tissue and to provide a positioning of the radioactive source at the desired location. The fixation element may include at least one barbed protrusion on the insertable member. The radioactive source may be completely encapsulated in the insertable member or the fixation element.

According further to the system described herein, a method for performing brachytherapy includes identifying an area of tissue for brachytherapy. An implantable device is inserted into the area of the tissue, in which the implantable device includes a fixation element and a radioactive source encapsulated within the implantable device. The implantable device is fixedly disposed using the at least one fixation element such that the radioactive source is fixed in a position for delivering radiation therapy to the desired tissue. The implantable device may be made of a memory alloy, and in which the implantable device is fixedly disposed by thermal processing after inserting the implantable device into the area of the tissue. The implantable device may have a helical coil shape that enables twisting of the insertable member for insertion of the implantable device in the tissue and to provide a desired positioning of the radioactive source. The insertable member may further includes at least one barbed protrusion on at least one end of the insertable member.

BRIEF DESCRIPTION OF THE DRAWINGS

Embodiments of the system described herein will now be explained in more detail in accordance with the figures of the drawings, which are briefly explained as follows.

DETAILED DESCRIPTION OF VARIOUS EMBODIMENTS

The system described herein provides for devices and techniques for permanent application of radioactive sources in the field of brachytherapy. In an embodiment, an implantable device for radiation therapy of pathological tissues directed toward the administration of radiation to tissue adjacent a cavity wall or surgical excision. The device may include an insertable member, such as a substantially cylindrical member, having at least two ends, such as opposing ends, a central section positioned between the ends, and a fixation element to retain the implantable device implanted in tissue at a desired position. The device may further include a radioactive source at least partially positioned within the insertable member and that is disposed to deliver radiation to a desired area.

The radioactive source may be encapsulated by an outer portion of the insertable member, e.g., positioned in a chamber spatially located from a periphery of the outer portion. A radioactive source may be a radioactive nuclide that decays by electron capture without the emission of beta particles or may be a radioactive nuclide that decays with the emission of beta particles. Such a radioactive nuclide may decay with the emission of gamma rays and/or X-rays, for example, having a weighted average energy from about 20 keV to about 100 keV. The radioactive nuclide may be selected from palladium-103, iodine-125, gadolinium-153, samarium-145, cesium-131 and ytterbium-169.

In accordance with another embodiment, the system described herein provides a method for the treatment of tissue adjacent a cavity wall. Such a method may include identifying a cavity within a body of tissue, e.g., by removing a portion of tumorous tissue within a body of tissue so as to generate a cavity. The method may also include placing within the remaining adjacent tissue an implantable device, such as described elsewhere herein, having a fixation and at least one radioactive source, e.g., in which the outer portion has a fixation sufficient for implantation adjacent to or into the cavity wall, and the radioactive source is positioned within an area spatially located from a periphery of the outer portion for delivering radiation therapy to the tissue adjacent the cavity wall.

Figure 1A:
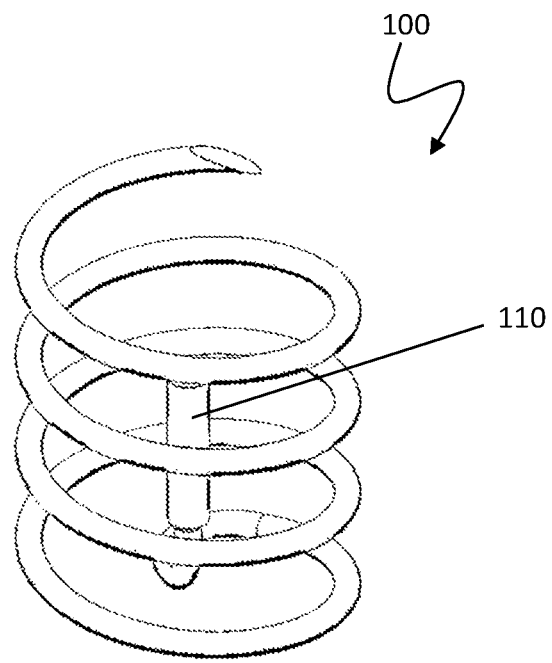
FIGS. 1A and 1B are schematic illustrations of an implantable device in the form of a helical coil which contains an encapsulated radioactive source according to an embodiment of the system described herein.
Figure 1B:
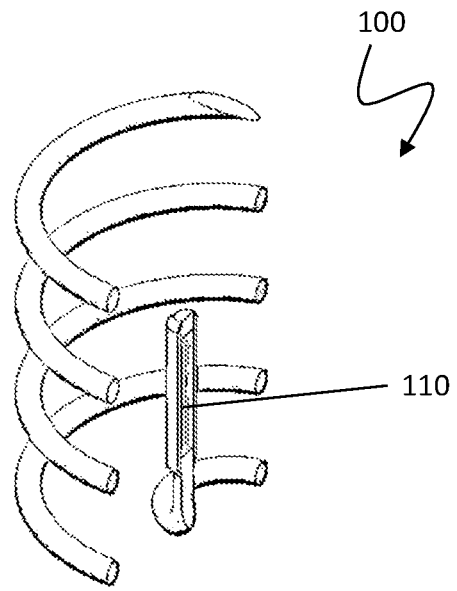

FIGS. 1A and 1B are schematic illustrations of an implantable device in the form of a helical coil 100 (e.g., a helical clip or tack) which contains an encapsulated radioactive source 110 according to an embodiment of the system described herein. FIG. 1B is a section view of the helical coil 100 shown in FIG. 1A. In the illustrated embodiment, the helical coil 100 is substantially cylindrical member having at least two ends, a central section positioned between the ends, and a fixation element in the form of the helical coiled configuration of the coil 100. The radioactive source 110 may be incorporated into and/or onto the helical coil 100 such that it may be rotated into and through a thin segment of tissue. In various embodiments, the source 110 may be located at the end of the helical coil 110 and/or located between the ends of the coil 100. The coil 100 may be affixed to tissue by engaging the leading end of the coil 100, that may be sharpened or pointed, through a segment of tissue and then rotating the coil 100 to cause additional material to pass through the tissue.

In an embodiment, the coil 100 may be made from any implantable material including "memory" alloys such as a Nickel Titanium or nitinol. The coil made from memory metal may be made to tighten its hold on tissue after implantation due to thermal transition. The transition may also enable hiding the pointed end of the coil 100 to keep it from piercing unintended targets. The coil 100 may even be implanted while at a temperature below ambient room, and well below body temperature, to maximize the thermal-mechanical transition. This would be beneficial for very thin tissues and also for locations that are prone to cyclic motion due to normal body functions such as general mobility & bodily functions like swallowing, pumping blood, and digesting.

In various embodiments, the nitinol may be used in contact with the body tissue, or it may be coated, clad or otherwise covered to provide for more lubricious (slippery) coating for ease of application, or a more resistive coating to resist migration. Further, the nitinol may serve as the primary encapsulation of the radioactivity, or it may serve as an outer carrier for a previously encapsulated radioactive source.

Figure 2A:
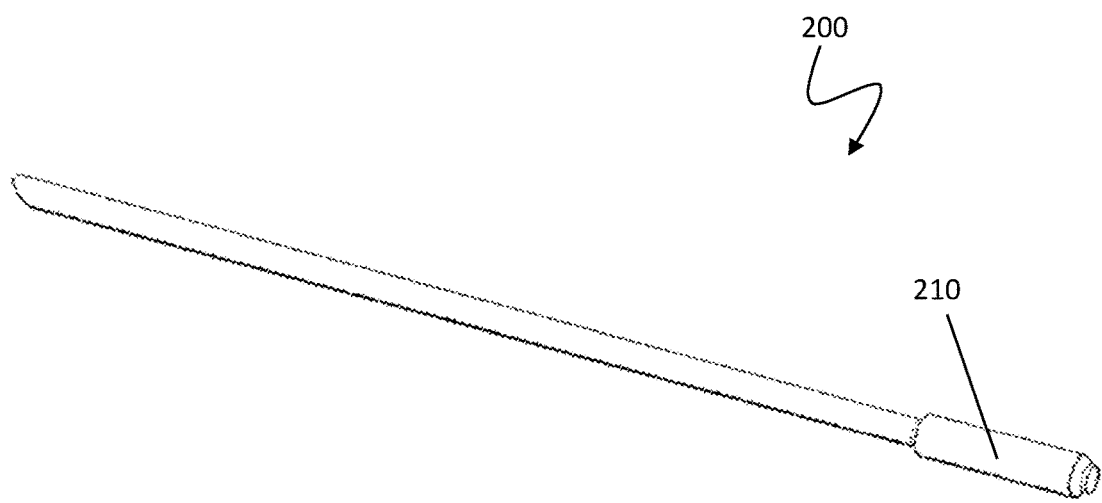
FIGS. 2A and 2B are schematic illustrations showing another embodiment of the system described herein for an implantable device in which a single wire is made from implantable memory alloy.
Figure 2B:
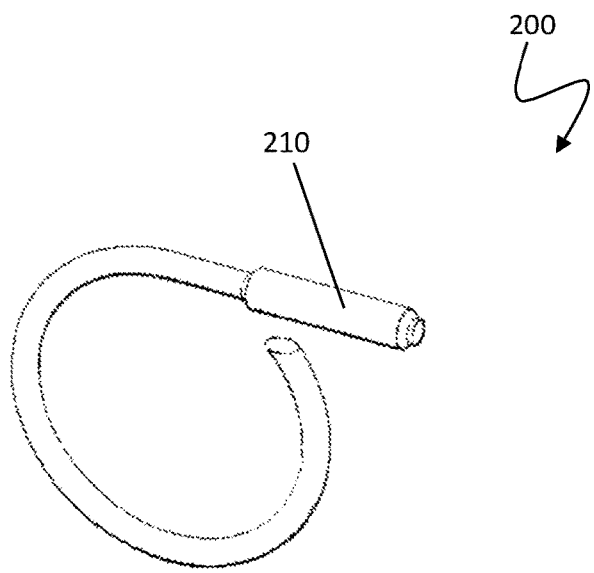

FIGS. 2A and 2B are schematic illustrations showing another embodiment of the system described herein for an implantable device in which a single wire 200 is made from implantable memory alloy such as a Nickel Titanium or nitinol. FIG. 2B is a view of the single wire shown in FIG. 2A after the memory alloy has been bent into a non-straight configuration according to shape-memory of the alloy. The single wire may be inserted into tissue in the straight configuration at room temperature and bend into the non-straight configuration when reaching normal body temperature, thereby establishing its hold on tissue after insertion due to thermal transition. In the illustrated embodiment, an encapsulated radioactive source 210 may be incorporated into and/or onto the single wire 200. In various embodiments, the nitinol may serve as the primary encapsulation of the radioactivity, or it may serve as an outer carrier for a previously encapsulated radioactive source. As discussed elsewhere herein, the nitinol may be used in contact with the body tissue, or it may be coated, clad or otherwise covered to provide for more lubricious (slippery) coating for ease of application, or a more resistive coating to resist migration. In addition to the use of nitinol for shape-memory configuration of the device, this thermal transition fixation may be achieved using a more traditional bi-metallic junction such as is employed in a typical thermostat or thermal switch.

Figure 3A:
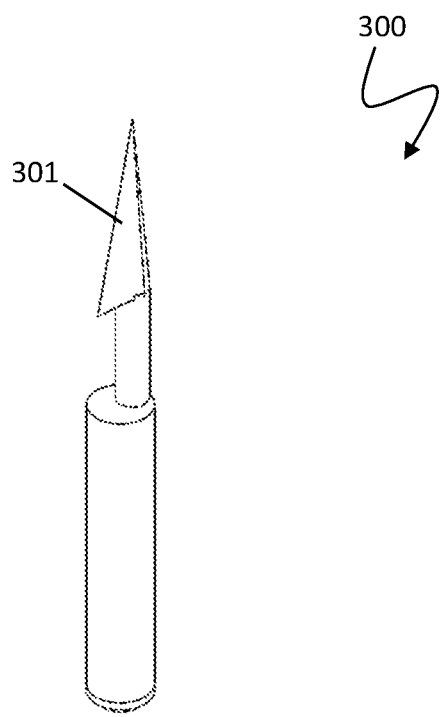
FIGS. 3A and 3B are schematic illustrations showing another embodiment of the system described herein as a barbed holder that may have an encapsulated radioactive source.
Figure 3B:
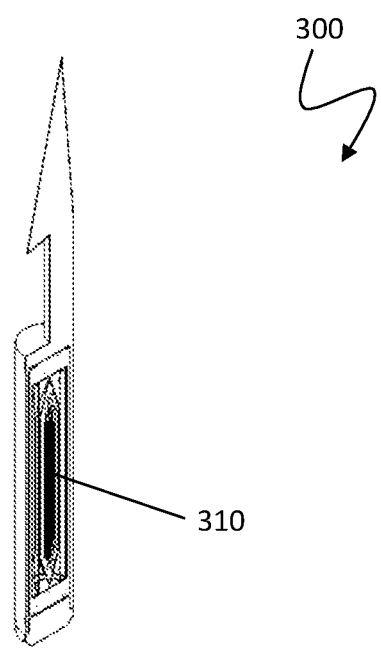

FIGS. 3A and 3B are schematic illustrations showing another embodiment of the system described herein as a barbed holder (and/or harpoon) 300 that may have an encapsulated radioactive source 310, for example, incorporated as a capsule appended thereto, and/or otherwise attached to the barbed holder 300, such that the barbed holder 300, with appended radioactive source 310, may pushed into and through a thin segment of tissue. FIG. 3B is a section view of the barbed holder 300 shown in FIG. 3A. The barbed holder 300 may be affixed to tissue by pushing the leading (pointed) end of the barbed holder 300 through a segment of tissue and one or more barbs 301 would cause resistance to removal through the aperture created by the deployment. In the illustrated embodiment, the encapsulated radioactive source 310 is shown completely encapsulated within the barbed holder 300. Although the figure shows the encapsulated radioactive source 310 attached to one end of the barbed holder 300, it is noted that the encapsulated radioactive source may be attached to a side of the barbed holder 300, and that the barbed holder 300 may be aligned parallel to the axis of the encapsulation, aligned perpendicular to the axis of the encapsulation and/or aligned at any angle between parallel and perpendicular.

Figure 4A:
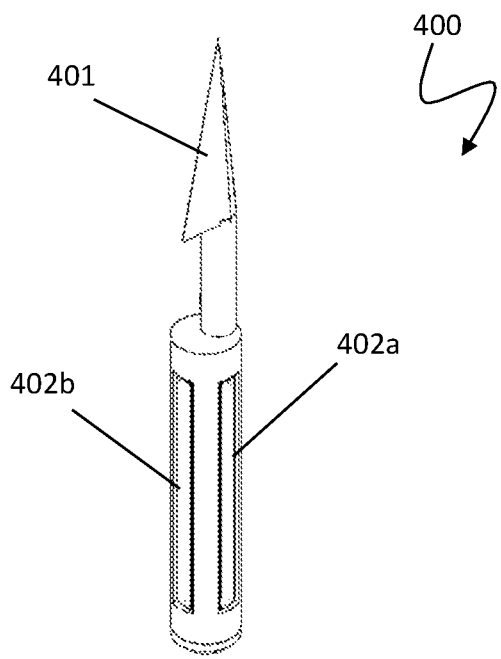
FIGS. 4A and 4B are schematic illustrations showing a barbed holder with cut-outs or windows which contain an encapsulated radioactive source according to another embodiment of the system described herein.
Figure 4B:
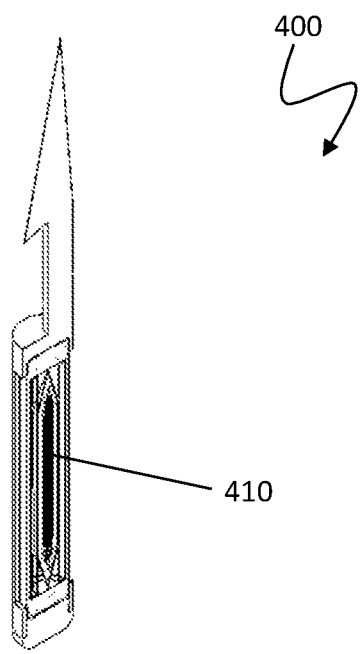

FIGS. 4A and 4B are schematic illustrations showing a barbed holder 400 with cut-outs or windows 402 which contain an encapsulated radioactive source 410 according to another embodiment of the system described herein. FIG. 4B shows a section view of the barbed holder 400 of FIG. 4A. The holder 400 may include one or more barbs 401, like that discussed in connection with the holder 300, but, rather than requiring complete encapsulation of the radioactive source 410, it is possible for the holder 400 to engage only one end of the radioactive source 410, or engage both ends, with cut-outs or windows 402a, 402b in the sides of the holder 400.

Figure 5A:
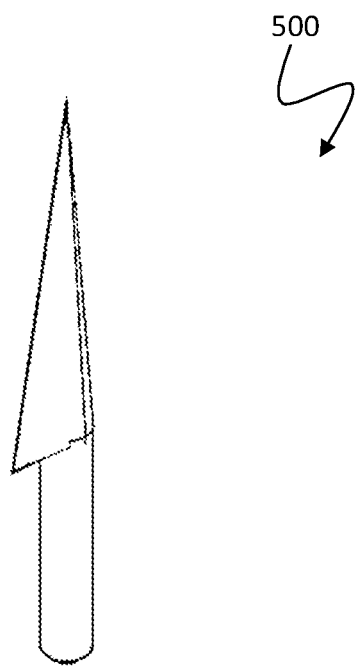
FIGS. 5A and 5B are schematic illustrations showing a barbed holder in which is incorporated a radioactive element such that the barbed holder itself becomes an encapsulated radioactive source according to an embodiment of the system described herein.
Figure 5B:
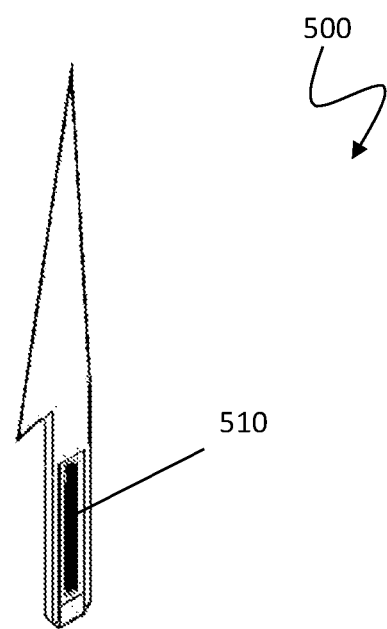

FIGS. 5A and 5B are schematic illustrations showing a barbed holder 500 in which is incorporated a radioactive source element 510 such that the barbed holder itself becomes an encapsulated radioactive source according to an embodiment of the system described herein. FIG. 5B shows a section view of the barbed holder 500 shown in FIG. 5A. In the illustrated embodiment, by incorporating radioactivity into the barbed holder 500, such that the radioactive element 510 is inside the body of the holder 500, the barbed holder 500 as encapsulated source may be pushed into and through a thin segment of tissue. The holder 500 would be affixed to tissue by pushing the leading (pointed) end of the holder through a segment of tissue and the barb would cause resistance to removal through the aperture created by the deployment. In this embodiment, the barbed holder 500 itself, and/or at least a portion of the barbed protrusion of the barbed holder 500 in which the radioactive source is encapsulated, thereby becomes the brachytherapy source.

Figure 6:
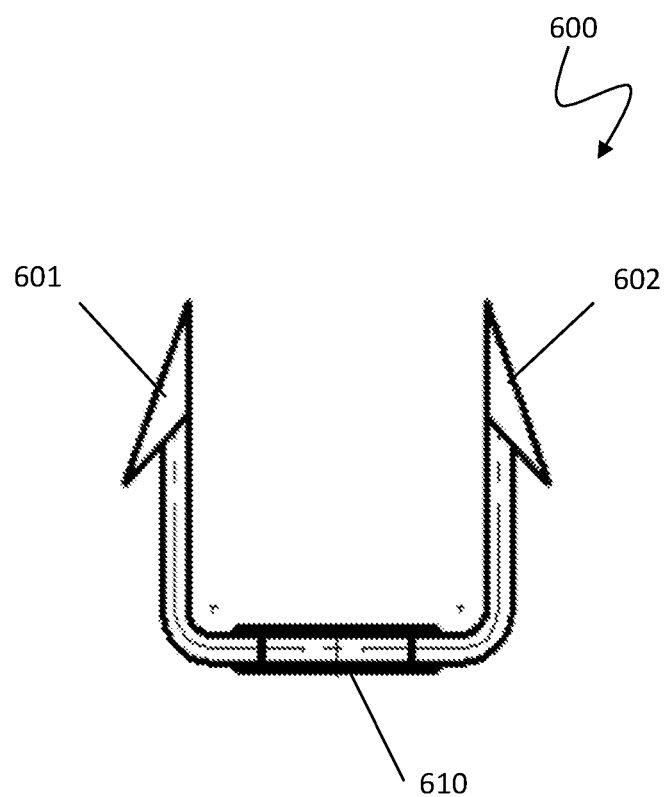
FIG. 6 is a schematic illustration showing shows multiple barbs of a barbed holder protruding in multiple directions according to an embodiment of the system described herein.

FIG. 6 is a schematic illustration showing shows multiple barbs of a barbed holder 600 protruding in multiple directions according to an embodiment of the system described herein. For example, the barbed holder 600 may have two barbs 601, 602 positioned on either side of an encapsulated radioactive source 610. In an embodiment, as illustrated, the barbed holder 600 may be bent along its length (staple-like) to permit both barbs 601, 602 to be simultaneously engaged. In other embodiments, the barbed holder 600 may not be bent and/or may be bent in other directions, and, in yet other embodiments, the barbed holder 600 may have barbs protruding from the encapsulated source 610 in multiple directions. In an embodiment, a staple clip may be fabricated by welding a 0.25 mm diameter wire axially parallel to the leg of the clip. The pointed end may be cut with wire clippers and then ground using a fine grinding stone attachment to a grinding device.

Figure 7:
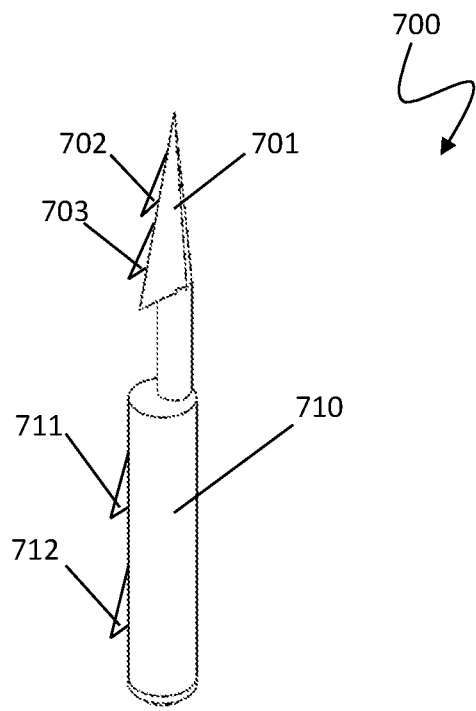
FIG. 7 is a schematic illustration of a barbed holder having multiple barbs in an array on one side of the barbed holder according to another embodiment of the system described herein.

FIG. 7 is a schematic illustration of a barbed holder 700 having multiple barbs 701, 702, 703 in an array on one side of the barbed holder 700 according to another embodiment of the system described herein. In various embodiments, the multiple barbs 701, 702, 703 may be on one or both ends. The illustrated embodiment shows an array of barbs 701, 702, 703 protruding from one side of the holder 700. Additionally, the illustrated embodiment shows additionally and/or alternatively multiple barbs 711, 712 protruding from an encapsulated radioactive source 710 of the holder 700.

Figure 8:
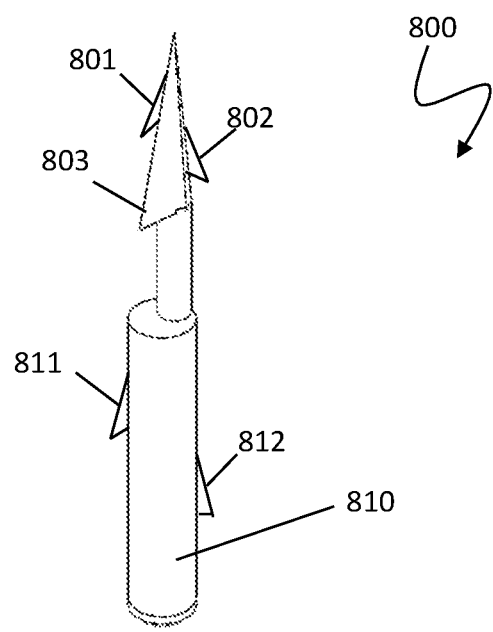
FIG. 8 is a schematic illustration of a barbed holder having multiple barbs protruding in multiple directions from the barbed holder according to an embodiment of the system described herein.

FIG. 8 is a schematic illustration of a barbed holder 800 having multiple barbs 801, 802, 803 protruding in multiple directions from the barbed holder according to an embodiment of the system described herein. In various embodiments, the multiple barbs 801, 802, 803 may be on one or both ends, and the barbs 801, 802, 803 may be disposed in different locations and orientations. The illustrated embodiment shows an array of barbs 701, 702, 703 protruding from multiple sections of the holder 800. Additionally, the illustrated embodiment shows additionally and/or alternatively multiple barbs 811, 812 protruding in different directions from an encapsulated radioactive source 810 of the holder 800.

Figure 9:
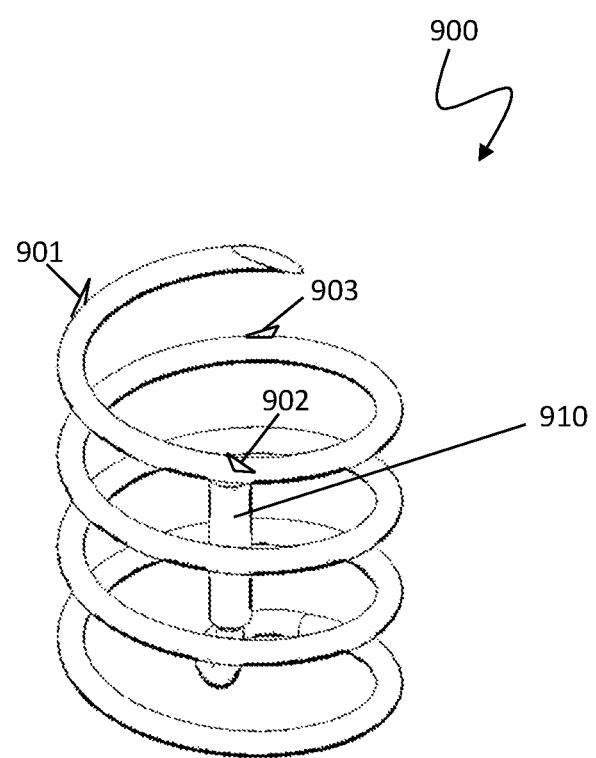
FIG. 9 is a schematic illustration of a barbed holder comprised of multiple barbs disposed on a helical coil like that described elsewhere herein to prevent the coil, with encapsulated radioactive source, from unscrewing and/or otherwise dislodging from the tissue according to an embodiment of the system described herein.

FIG. 9 is a schematic illustration of a barbed holder 800 comprised of multiple barbs 901, 902, 903 disposed on a helical coil like that described elsewhere herein to prevent the coil, with encapsulated radioactive source 910, from unscrewing and/or otherwise dislodging from the tissue according to an embodiment of the system described herein.

In various embodiment, the helical coil embodiment as illustrated may be fabricated from a single length of wire by bending and coiling the wire into the desired configuration with the radioactive encapsulation attached at one end. Alternatively, the helical coil embodiment maybe fabricated from one length of wire by bending and coiling the wire into the desired configuration with the radioactive encapsulation attached at one end, and with another length of wire, bent and coiled to the desired configuration, attached to the other end. In other embodiments, the helical coil and/or barbed holder embodiments may be fabricated by casting metal into a desired shape, by molding a polymer material into the desired shape, by 3D printing from metal, plastic, or a combination, and/or by being over-molded onto an existing device, among other possible fabrication techniques.

The barbed protrusions may also be fabricated in a variety of ways. In one embodiment, the barb can be fabricated by machining from a solid piece of material. Alternatively, the barbed protrusion may be fabricated by casting metal into the desired shape. Alternatively, the barbed protrusion may be fabricated by molding a polymer into the desired shape, by roll-forming, and/or by stamping, among other possible fabrication techniques.

Figures 10A, 10B, 10C:
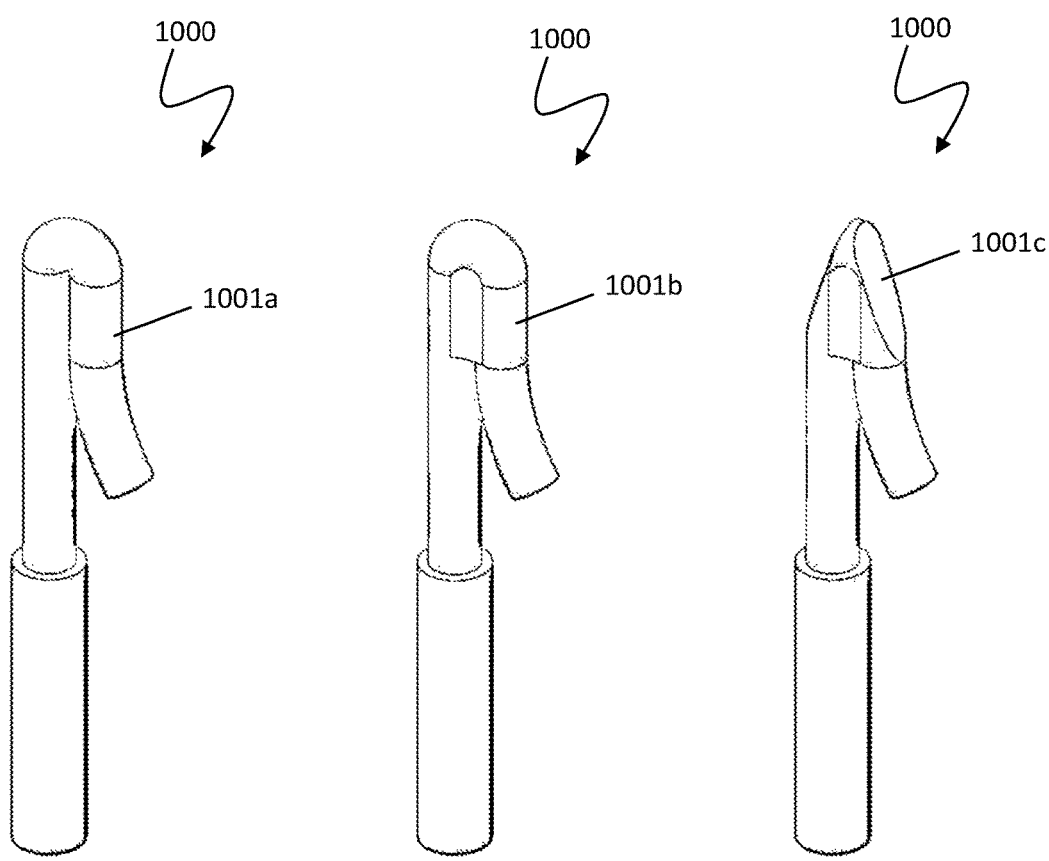
FIGS. 10A-10C shows formation of a barbed protrusion on a barbed holder according to an embodiment of the system described herein.

FIGS. 10A-10C shows formation of a barbed protrusion on a barbed holder 1000 according to an embodiment of the system described herein. A barbed protrusion 1001a may be initially formed by bending a protruding wire back upon itself (FIG. 10A). The two now-parallel wires of the protrusion 1001b may be welded together over a short distance (FIG. 10B). The end can then be ground or possibly shaped by laser cutting, or by machining to form the finalized barbed protrusion 1001c (FIG. 10C).

Figure 11:
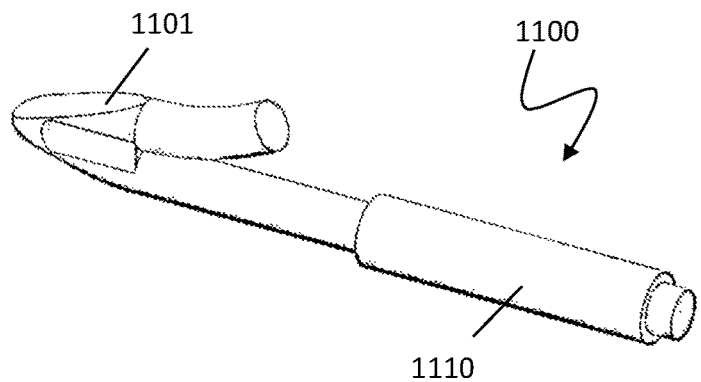
FIG. 11 is a schematic illustration showing that a barbed protrusion may be formed on one end of a barbed holder and the other end of the holder, with a radioactive source therebetween, being simply plugged according to an embodiment of the system described herein.

FIG. 11 is a schematic illustration showing that a barbed protrusion 1101 may be formed on one end of a barbed holder 1100 and the other end of the holder 1100, with a radioactive source 1110 therebetween, being simply plugged according to an embodiment of the system described herein.

Figure 12:
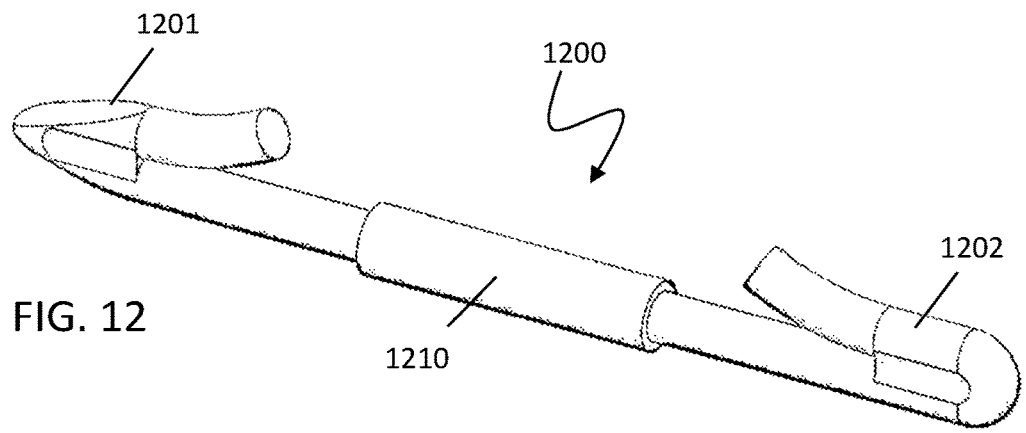
FIG. 12 is a schematic illustration showing a barbed holder with multiple end protrusions according to an embodiment of the system described herein.

FIG. 12 is a schematic illustration showing a barbed holder 1200 with multiple end protrusions 1201, 1202 according to an embodiment of the system described herein. The protrusion 1201 may be barbed for insertion of the holder 1200 and radioactive source 1210 into tissue as discussed elsewhere herein. In order to preclude the radioactive source migrating in the forward direction because of lack of any retarding resistance, the protrusion 1202 may be formed from a second bent wire incorporated onto the opposite end. In this embodiment, the protrusion 1201 may be required to be sharp, as it would not be used for piercing the tissue, but only for retarding further forward movement.

Figure 13:
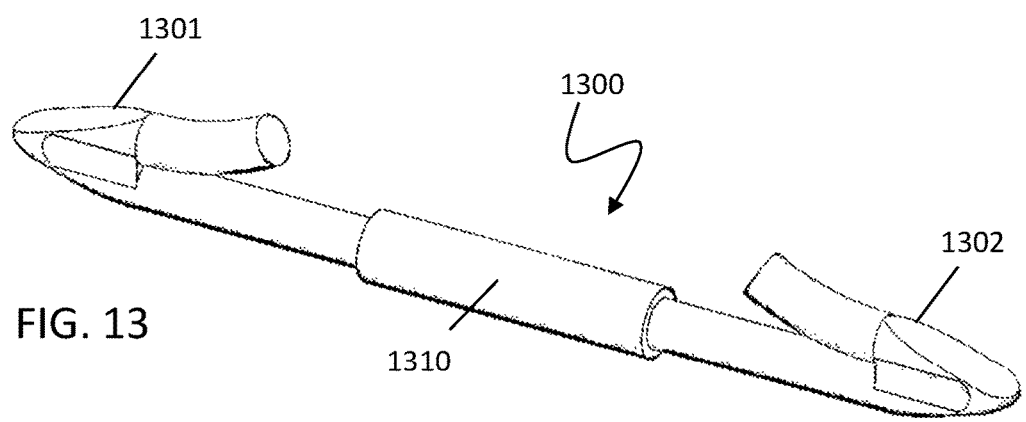
FIG. 13 is a schematic illustration showing a barbed holder showing multiple protrusions in which both of the protrusions are formed to be pointed, which would permit the holder and radioactive source to be inserted in either direction according to an embodiment of the system described herein.

FIG. 13 is a schematic illustration showing a barbed holder 1300 showing multiple protrusions 1301, 1302 in which both of the protrusions 1301, 1302 are formed to be pointed, which would permit the holder 1300 and radioactive source 1310 to be inserted in either direction according to an embodiment of the system described herein. This embodiment may advantageously eliminate the need for orientation in the delivery needle.

Figures 14A, 14B, 14C:
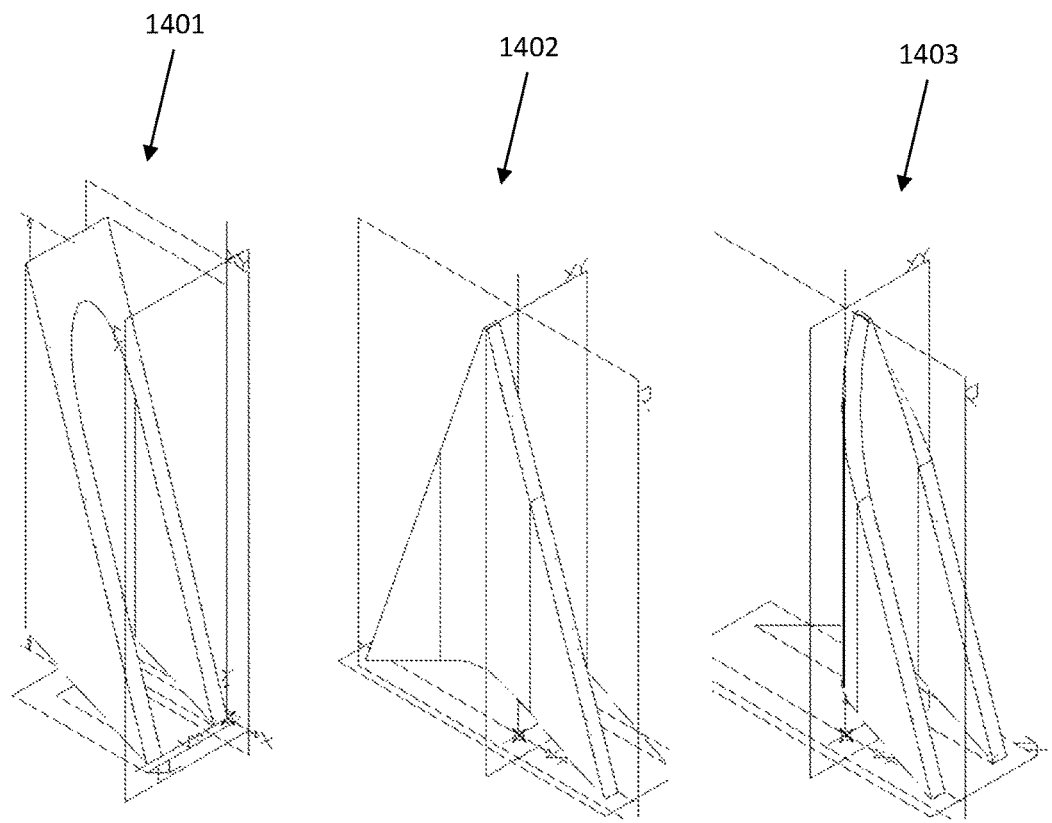
FIGS. 14A-14C are schematic illustrations showing embodiments for fabrication of a barb for a barbed holder according to the system described herein.

FIGS. 14A-14C are schematic illustrations showing embodiments for fabrication of a barb for a barbed holder according to the system described herein. FIG. 14A shows that a barb 1401 may be fabricated by machining to its final configuration. Alternatively, as shown in FIG. 14B, a barb 1402 could be fabricated by machining, or cutting, or stamping in a flat configuration. As shown in FIG. 14C, a barb 1403 may then be manufactured by further bending the barb 1402 into a final desired shape.

Figure 15A:
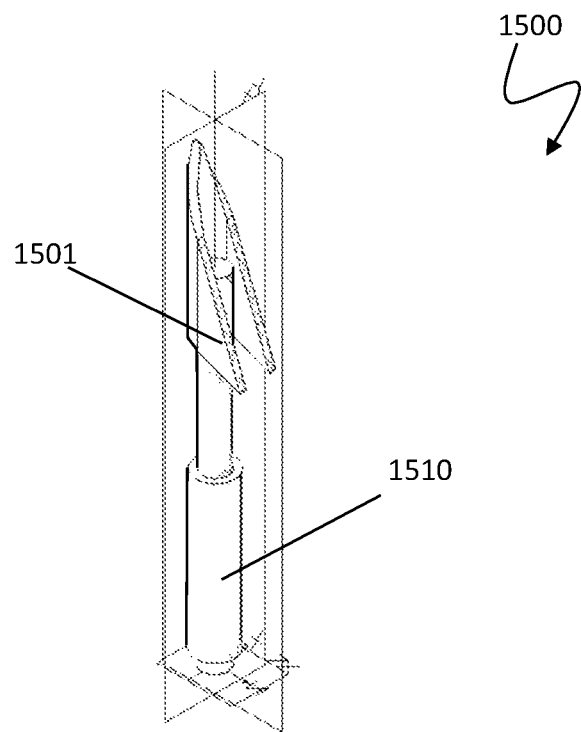
FIGS. 15A and 15B shows a barbed holder in which a barb is attached to the holder by welding to a protrusion from the body of the source encapsulation according to an embodiment of the system described herein.
Figure 15B:
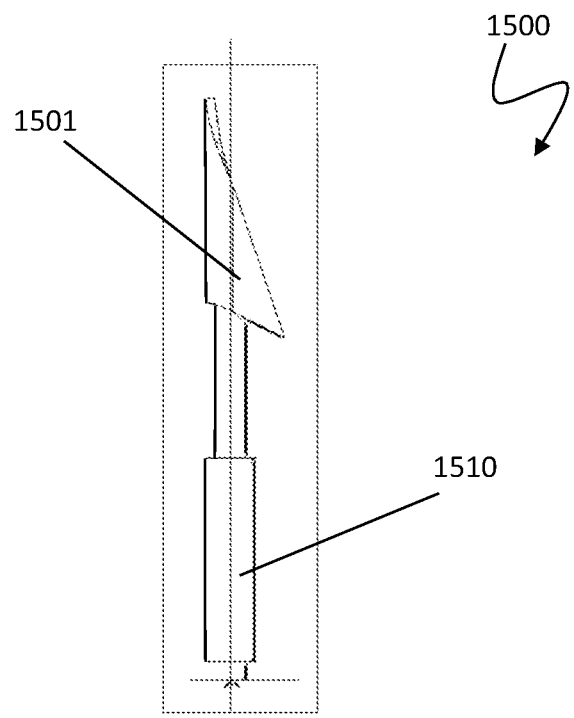

FIGS. 15A and 15B shows a barbed holder 1500 in which a barb is attached to the holder 1500 by welding to a protrusion from the body of the source encapsulation according to an embodiment of the system described herein. FIG. 15B shows a side view of the barbed holder or harpoon of FIG. 15A. The barbed holder 1500 is appended to an encapsulated radioactive source 1510.

Figure 16:
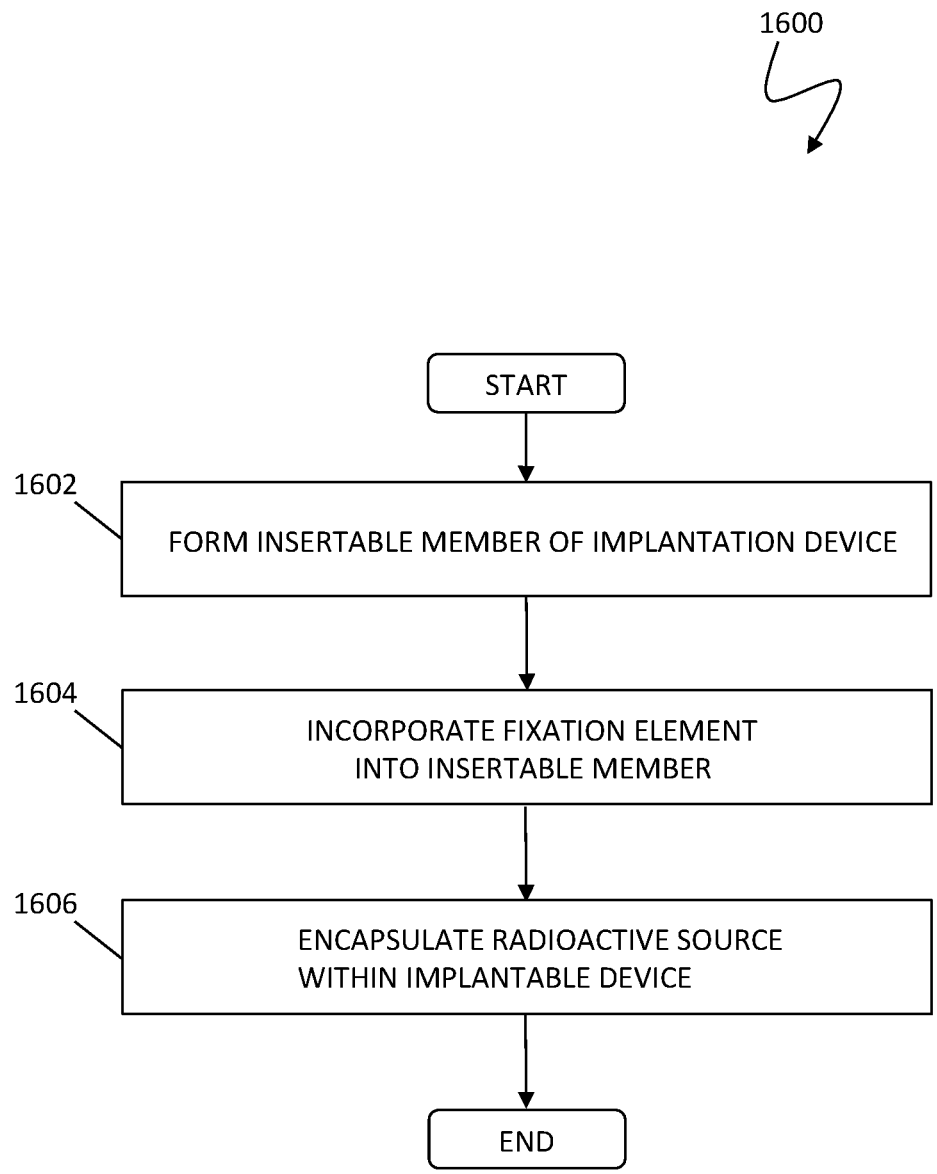
FIG. 16 is a flow diagram for a method for producing an implantable device for brachytherapy according to one or more embodiments of the system described herein.

FIG. 16 is a flow diagram 1600 for a method for producing an implantable device for brachytherapy according to one or more embodiments of the system described herein. At a step 1602, an insertable member of the implantable device is formed from material that is suitable for insertion into desired tissue for brachytherapy. In various embodiments, the insertable member may be substantially cylindrical and may be made of a single wire and/or may be a harpoon shape. After the step 1602, at a step 1604, a fixation element is incorporated into and/or affixed to the insertable member. In various embodiments, the fixation element may be a helical coil shape configuration of the insertable member and/or may be at least one barbed protrusion affixed to at least section of the insertable member. In other embodiments, the fixation element may result from a memory alloy material of which the insertable member is manufactured, such that the fixation element of the insertable member is the shape into which the insertable member forms after implantation of the implantation device. After the step 1604, at a step 1606, a radioactive source is encapsulated into the implantable device. In various embodiments, the radioactive source may be completely or partially encapsulated within the insertable member, such as within a chamber thereof and/or otherwise incorporated into and/or appended to the insertable member. In other embodiments, the radioactive source may be completely or partially encapsulated within the fixation element. It is noted that any of the above-noted steps may be performed in a different order. After the step 1606, processing is complete.

Figure 17:
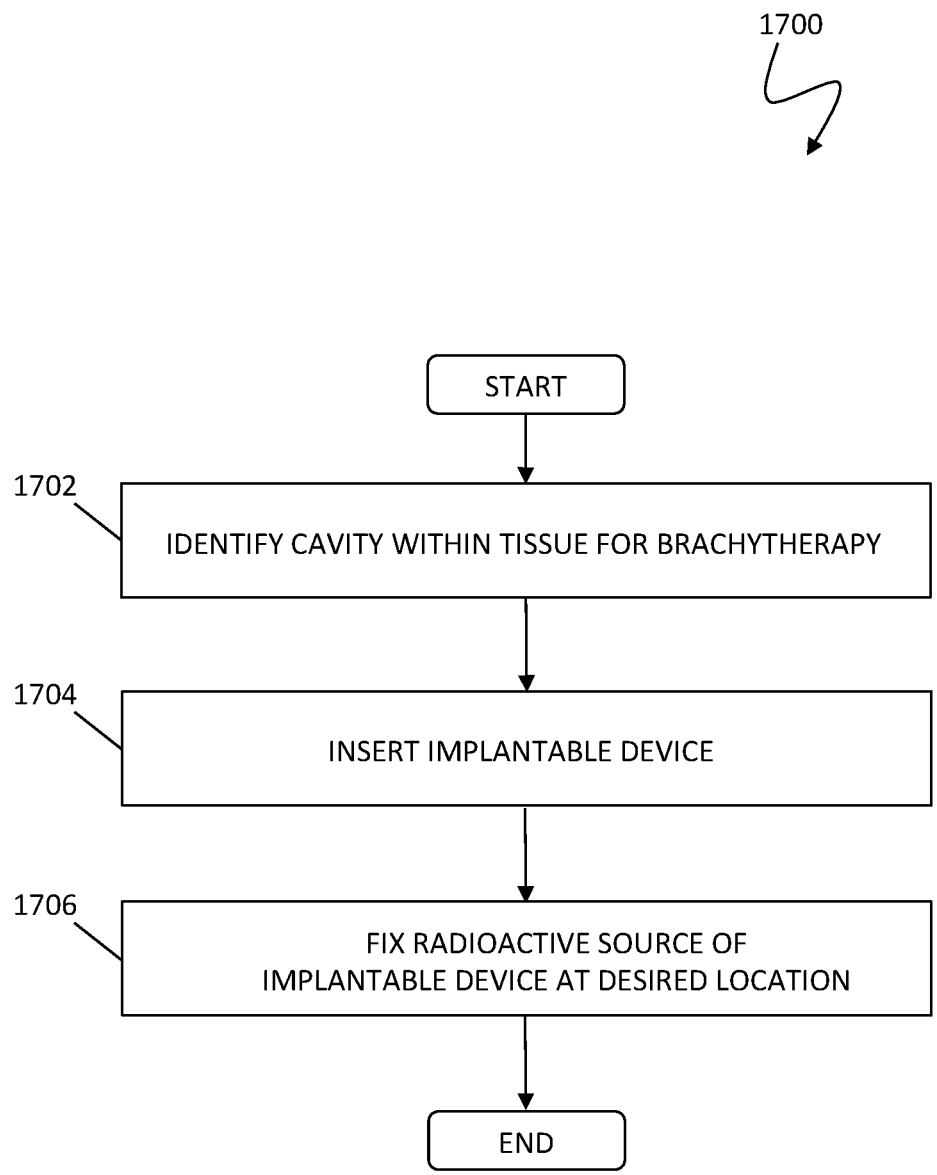
FIG. 17 is a flow diagram for a method for brachytherapy according to an embodiment of the system described herein.

FIG. 17 is a flow diagram 1700 for a method for brachytherapy according to an embodiment of the system described herein. At a step 1702, a cavity within a body of tissue is identified. For example, a portion of tumorous tissue within a body of tissue may be removed so as to generate the cavity. After the step 1702, at a step 1704, an implantable device is inserted into or adjacent to the cavity. The implantable device may be formed and/or configured as one or more of the embodiments discussed herein and, specifically, may having a fixation element and at least one radioactive source encapsulated within the implantable device, as discussed in detail elsewhere herein. After the step 1704, at a step 1706, the implantable device is fixedly disposed such that the radioactive source is positioned for delivering radiation therapy to the desired tissue. The fixation element and the radioactive source may be implemented as one or more of the embodiments discussed herein. For example, the fixation may occur as a result of post-implantation thermal processing where the implantable device is made of a memory alloy. After the step 1706, processing is complete.

In another embodiment of the system described herein, one or more components of the implantable device, e.g., the insertable member holding the radioactive source and/or one or more elements of the insertable member, may be a bio-resorbable component made of a bio-resorbable material. In this example, the one or more bio-resorbable components of the implantable device may dissolve and/or be absorbed in the body after the therapeutic dose has been delivered. This embodiment using the one or more bio-resorbable components may be appropriately used in connection with any one of more of the embodiments of the system described herein.

In yet another embodiment of the system described herein, one or more components of the implantable device, e.g., the insertable member holding the radioactive source and/or any one or more elements of the insertable member, may include a drug eluting component, such as a drug eluting member and/or a drug eluting device. In this example, the drug eluting component of the implantable device may provide drugs to enhance the radiation dose effects to cancer cells and/or provide drugs to protect healthy cells from the radiation doses of the implantable device. This embodiment using the drug eluting component may be appropriately used in connection with any one of more of the embodiments of the system described herein.

Various embodiments discussed herein may be combined with each other in appropriate combinations in connection with the system described herein. Additionally, in some instances, the order of steps in the flow diagrams, flowcharts and/or described flow processing may be modified, where appropriate. Further, it is noted that various aspects of the system described herein may be implemented using software, hardware, a combination of software and hardware and/or other computer-implemented modules or devices having the described features and performing the described functions. For example, aspects of manufacture of the system described herein and/or of implanting of the implantable device at desired locations according to the embodiments of the system described herein may be implemented in connection with the use of software and/or other computer components to provide levels of design or control of aspects of the system described herein. In this regard, software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An implantable device for brachytherapy, comprising:
   an insertable member having a first end and a second end, a central section positioned between the ends, and a fixation element having at least one barbed protrusion that resists removal through an aperture created by deployment to retain the implantable device in an inserted position within tissue; and
   a radioactive source disposed within the insertable member, wherein the insertable member is made of a memory alloy, and wherein the fixation element includes a non-straight configuration into which the insertable member forms after insertion into the inserted position and wherein the radioactive source is encapsulated within the fixation element.

2. The implantable device according to claim 1, wherein the memory alloy is Nickel Titanium or nitinol.

3. The implantable device according to claim 1, wherein the fixation element includes a plurality of barbed protrusions on the insertable member.

4. The implantable device according to claim 1, wherein the radioactive source is encapsulated within the insertable member.

5. The implantable device according to claim 4, wherein the radioactive source is completely encapsulated within the insertable member.

6. The implantable device according to claim 4, wherein the insertable member includes a chamber with at least one cut-out for external accessibility, and wherein the radioactive source is partially encapsulated within the insertable member by being disposed within the chamber with the at least one cut-out.

7. The implantable device according to claim 1, wherein the radioactive source includes a radioactive nuclide selected from at least one of: palladium-103, iodine-125, gadolinium-153, samarium-145, cesium-131 or ytterbium-169.

8. The implantable device according to claim 1, wherein the insertable member includes at least one of: a bio-resorbable component or a drug eluting component.

9. A method of manufacturing an implantable device for brachytherapy, comprising:
   forming an insertable member of the implantable device for insertion into an area of tissue;
   encapsulating a radioactive source in the implantable device; and
   incorporating a fixation element having at least one barbed protrusion that resists removal through an aperture created by deployment to retain the implantable device in an inserted position within tissue, wherein the insertable member is made of a memory alloy and wherein the fixation element includes a non-straight configuration into which the insertable member forms after insertion into the inserted position and wherein the radioactive source is encapsulated within the fixation element.

10. The method according to claim 9, wherein the radioactive source is completely encapsulated in the fixation element.

11. The method according to claim 9, wherein the memory alloy is Nickel Titanium or nitinol.

12. The method according to claim 9, wherein the radioactive source includes a radioactive nuclide selected from at least one of: palladium-103, iodine-125, gadolinium-153, samarium-145, cesium-131 or ytterbium-169.

13. The method according to claim 9, wherein the insertable member includes at least one of: a bio-resorbable component or a drug eluting component.

14. A method for performing brachytherapy, comprising:
identifying an area of tissue for brachytherapy;
inserting an implantable device into the area of the tissue, wherein the implantable device includes a radioactive source encapsulated within the implantable device and a fixation element having at least one barbed protrusion that resists removal through an aperture created by deployment to retain the implantable device in an inserted position within tissue; and
fixedly disposing the implantable device using the fixation element to deliver radiation therapy to an area of the tissue, wherein the implantable device is made of a memory alloy and wherein the fixation element includes a non-straight configuration into which the implantable device forms after insertion into the inserted position and wherein the radioactive source is encapsulated within the fixation element.

15. The method according to claim 14, wherein the memory alloy is Nickel Titanium or nitinol.

16. The method according to claim 14, wherein the fixation element includes a plurality of barbed protrusions on the insertable member.

17. The method according to claim 14, wherein the insertable member includes a chamber with at least one cut-out for external accessibility, and wherein the radioactive source is partially encapsulated within the fixation element by being disposed within the chamber with the at least one cut-out.

18. The method according to claim 14, wherein the radioactive source includes a radioactive nuclide selected from at least one of: palladium-103, iodine-125, gadolinium-153, samarium-145, cesium-131 or ytterbium-169.

19. The method according to claim 14, wherein the insertable member includes at least one of: a bio-resorbable component or a drug eluting component.

* * * * *